United States Patent [19]

Tucci

[11] Patent Number: 4,545,367
[45] Date of Patent: Oct. 8, 1985

[54] DETACHABLE BALLOON CATHETER AND METHOD OF USE

[75] Inventor: Charles A. Tucci, Miami, Fla.

[73] Assignee: Cordis Corporation, Miami, Fla.

[21] Appl. No.: 553,147

[22] Filed: Nov. 18, 1983

Related U.S. Application Data

[63] Continuation-in-part of Ser. No. 399,142, Jul. 16, 1982, abandoned.

[51] Int. Cl.⁴ ............................................ A61M 29/02
[52] U.S. Cl. ................................... 128/1 R; 128/325; 128/344; 604/96
[58] Field of Search ....................... 128/344, 325, 1 R; 604/96, 97, 98, 99, 102, 103, 104, 246, 247, 280, 283

[56] References Cited

U.S. PATENT DOCUMENTS

| | | | |
|---|---|---|---|
| 3,834,399 | 9/1974 | Hunter | 131/348 |
| 3,919,724 | 11/1975 | Sanders et al. | 3/36 |
| 4,029,104 | 6/1977 | Kerber | 128/348 |
| 4,085,757 | 4/1978 | Pevsner | 128/325 |
| 4,282,875 | 8/1981 | Serbineko et al. | 128/325 |
| 4,341,218 | 7/1982 | U | 128/325 |
| 4,364,392 | 12/1982 | Strother et al. | 128/325 |
| 4,370,982 | 2/1983 | Reilly | 604/99 X |

FOREIGN PATENT DOCUMENTS 2019219 10/1979 United Kingdom .
542523 7/1977 U.S.S.R. .

*Primary Examiner*—Michael H. Thaler
*Attorney, Agent, or Firm*—Henry W. Collins; Thomas R. Vigil

[57] ABSTRACT

The detachable balloon catheter assembly comprises a balloon and sealing valve assembly including a sealing valve being formed of a resilient material having an elongate passageway extending therethrough and being mounted in a sleeve, an inflatable balloon having a mouth portion which is bonded to the sealing valve, and a small diameter cannula having a distal end which extends through the passageway in the sealing valve. The small diameter cannula includes a connector terminal on the proximal end which is adapted to be coupled to a source of fluid pressure. The passageway in the sealing valve takes the form of an elongate slit prior to insertion of the small diameter cannula through the passageway, and upon insertion of the cannula through the passageway, the passageway takes the form of a cylindrical aperture which is in fluid-tight engagement with the outer surface of the cannula while allowing the cannula to easily slide through the passageway. When the balloon is inflated to a desired size, the cannula may be withdrawn from the passageway in the sealing valve thereby causing the passageway to revert to the slit configuration in order to provide a fluid-tight seal for the inflated balloon. In one embodiment, a piston is mounted on the small diameter cannula and an aperture extends through the side wall of the cannula so that a burst of fluid pressure may be applied to the piston causing it to be driven away from the sealing valve to drive the cannula out of engagement with the sealing valve for detachment of the cannula from the inflated sealed balloon.

29 Claims, 14 Drawing Figures

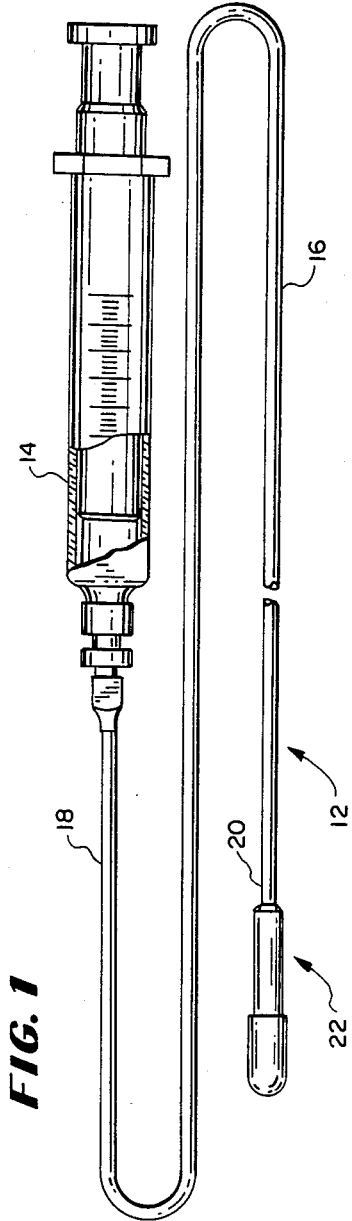
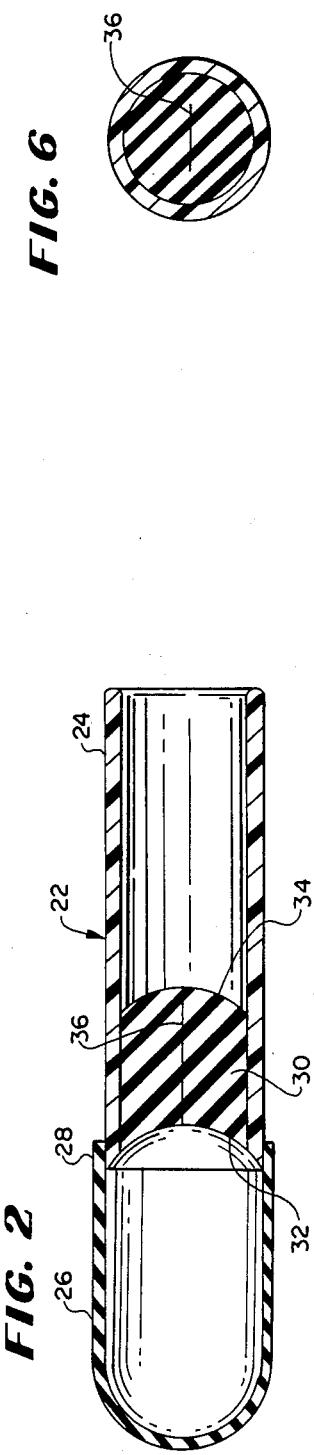
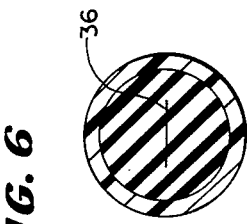

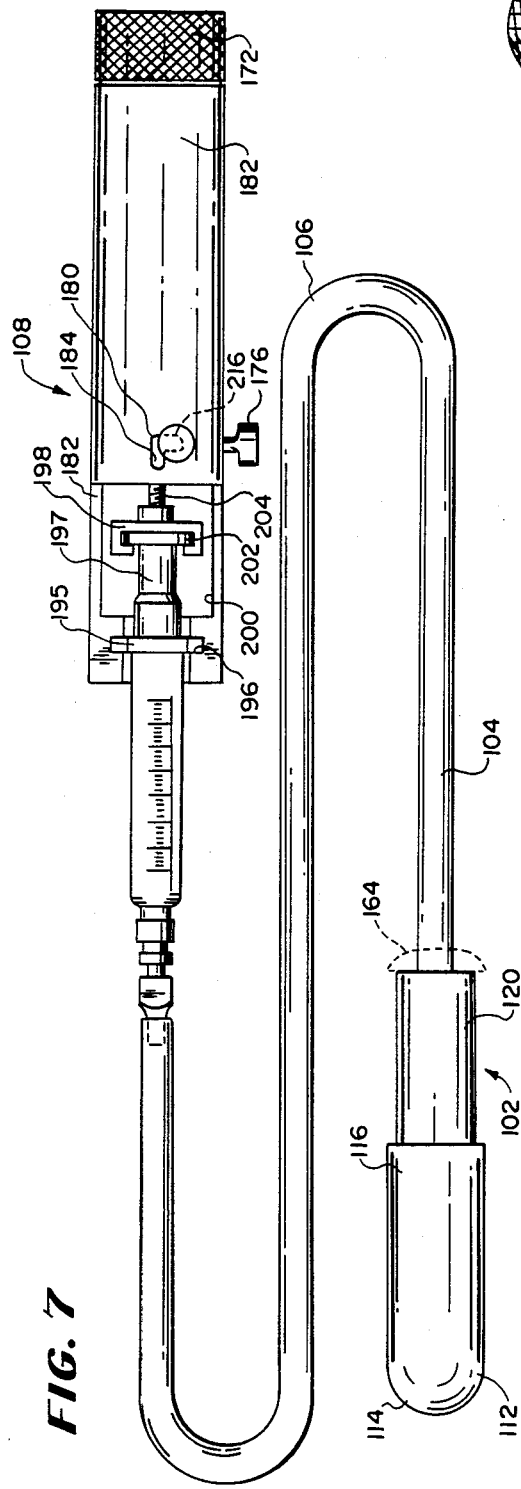
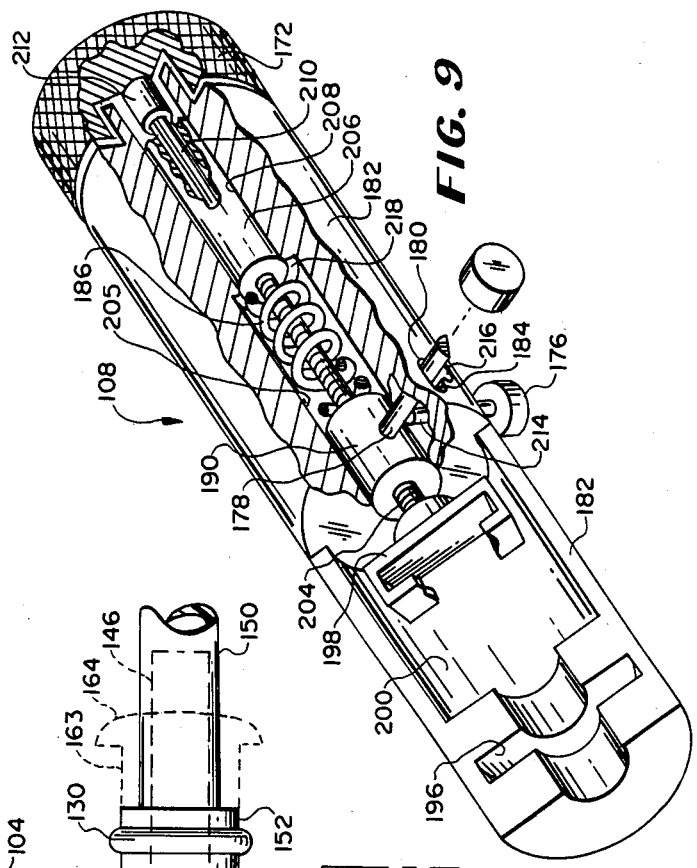
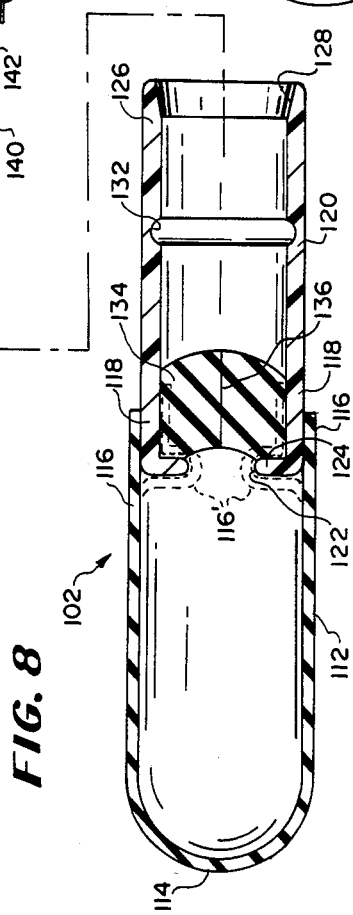

DETACHABLE BALLOON CATHETER AND METHOD OF USE

CROSS REFERENCE TO RELATED APPLICATION

This application is a continuation-in-part application of earlier U.S. application Ser. No. 399,142 filed on July 16, 1982 and entitled: Detachable Balloon Catheter now abandoned.

BACKGROUND OF THE INVENTION

1. Field of the Invention

The present invention relates to balloon catheters, and more particularly, to miniaturized detachable balloon catheters for use in blood vessels.

2. Description of the Prior Art

It has become a routine practice to use balloon catheters to occlude vessels in certain types of cardiovascular surgery. In this procedure, an inflatable balloon positioned on the distal end of a catheter with a cannula thereon is inserted into a blood vessel and is allowed to move to a proper position by circulation of blood through the vessel. At a desired location, the balloon is inflated by a fluid or by a solidifying filler material until the sides of the balloon are in contact with the walls of the blood vessel. The cannula is then withdrawn from the balloon and the balloon is left in the blood vessel in order to occlude the vessel.

One problem with such prior art detachable balloon catheters is that it is very difficult to precisely control the force required to withdraw the cannula from the balloon. As may be appreciated, if this force is too great, the balloon may be dislodged or repositioned in the blood vessel during detachment of the cannula. If the force required to withdraw the cannula from the balloon is too small, the balloon may become prematurely detached from the cannula during positioning of the balloon within the blood vessel.

Still another problem with such prior balloon catheters is that if a non-solidifying filler material, for example, a radiopaque iso-osmolal solution, is utilized to inflate the balloon, leakage of this material often occurs through the seal at the mouth of the balloon when the cannula is withdrawn from the balloon. Accordingly, an important objective of this invention is to provide a miniaturized detachable balloon catheter which may be used for permanent occlusion of a blood vessel, but one in which the inflatable balloon is not prematurely detached from the cannula.

Heretofore a number of catheter assemblies have been proposed and examples of some of these catheter assemblies are disclosed in the following patents:

U.S. Pat. No. 3,834,399 to Hunter; U.S. Pat. No. 3,919,724 to Sanders et al; U.S. Pat. No. 4,029,875 to Kerber; U.S. Pat. No. 4,085,757 to Pevsner; U.S. Pat. No. 4,282,875 to Serbinenko et al; U.S. Pat. No. 4,341,218 to Ü; U.S. Pat. No. 4,364,392 to Strother; U.K. Published Patent Application No. 2,019,219; and U.S.S.R. Inventor Certificate 542,523.

The Hunter et al U.S. Pat. No. 3,834,394 discloses a device for effecting occlusion of a blood vessel. The device is inserted into the desired blood vessel, moved to the desired point of occlusion and expanded at that site to a size greater than the diameter of the vessel so as to immovably retain the balloon therein. In one embodiment, the inserting catheter may be unscrewed from the balloon so as to leave the balloon in place.

The Sanders et al U.S. Pat. No. 3,919,724 discloses an implantable breast prosthesis which includes a flexible container having a self-sealing valve or plug. In one embodiment, the prosthesis is used in combination with a balloon catheter having an inflatable cuff.

The Kerber U.S. Pat. No. 4,029,104 discloses a calibrated leak balloon with a plug at the distal end of the balloon having a slit or restricted orifice cut through the plug to permit fluid to leak out of the balloon.

The Pevsner U.S. Pat. No. 4,085,757 discloses a miniature balloon catheter assembly which includes a cannula and an inflatable balloon constructed of a flexible material and detachably mounted on the distal end of the cannula. In one embodiment, the flexible tubing has a plug with a pin hole therein situated within the tubing between a closed distal end of the tubing and an open proximal end of the tubing. A resilient contracting member is received around the tubing and around the plug within the tubing. A hollow needle is mounted to the distal end of the cannula and extends into the flexible tubing with a point of the needle extending through the pin hole so that an open distal end of the needle is in communication with the balloon forming portion of the flexible tubing forward of the plug. The needle has a side opening therein located between the plug and the end of the cannula received in the open end of the flexible tubing. Preferably, an additional wire extends through the needle and terminates in a stop at the end thereof in the form of a sphere which can be drawn against the distal open end of the needle to stop flow of fluid into the balloon forming portion of the flexible tubing whereby further pressure would only be able to exit through the side opening to accomplish detachment by increasing the fluid pressure inside said flexible tubing to expand the proximal end of the tubing to release it from the cannula and to cause the contracting member to expand allowing the needle to be withdrawn after which the contracting member contracts around the tubing and plug to close the pin hole and seal the balloon.

As will be described in greater detail hereinafter, the miniature balloon catheter assembly disclosed in the Pevsner patent does not disclose or suggest a rigid cylinder within which a mouth of a balloon and a sealing valve are mounted, as provided in the balloon catheter assembly of the present invention.

The Serbinenko et al U.S. Pat. No. 4,282,875 discloses a detachable balloon removably attached to the end of a catheter by means of a bulbous portion on the catheter's end. In use, x-ray-TV is used to aid a surgeon in positioning the balloon in the lumen of a pathological vessel of the brain of a patient. By slightly pulling outward, the surgeon detaches the bulb or balloon and withdraws the catheter from the lumen of the vessel.

The Ü U.S. Pat. No. 4,341,218 discloses a detachable balloon catheter including a dual lumen catheter, one lumen for supplying fluid to a balloon and another lumen for supplying fluid pressure to an expandable balloon forming portion of the catheter adjacent the distal end thereof. A cylinder is mounted to and within the balloon and has a ball therein. An opening to the cylinder is provided and the distal end of the catheter is inserted through the opening into the cylinder and the balloon forming portion thereof is inflated to fix the distal end of the catheter in the cylinder.

After a sufficient amount of fluid is passed through the first lumen into the cylinder and then into the balloon, the pressure in the second lumen is decreased to deflate the balloon forming portion thereof so that the distal end of the catheter can be forced out of the cylinder by the ball which then seals the opening to the cylinder.

The Strother, et al. U.S. Pat. No. 4,364,392 discloses a detachable balloon catheter with a neck mounted in the mouth of the balloon. The neck has a pair of grooves therein and an end of a catheter received within the neck has a pair of ridges thereon for being received in the grooves. The mating of the ridges in the grooves serves to hold the distal end of the catheter within the neck within the mouth of the balloon while the balloon is being filled with pressurized fluid. Then, a second catheter received about the first catheter having the ridges thereon is moved relative to the first catheter to urge the distal end of the second catheter against the neck thereby to detach the neck from the distal end of the first catheter.

The U.K. Pat. Publ. No. 2,019,219 discloses a self-sealing connector for use with plastic cannulas and vessel catheters wherein the connector has a disc of elastic material mounted across a passageway through the connector and the disc has a slit therein which can be forced open by fluid pressure or a rigid tube allowing fluid to pass through the disc and through the passageway in the connector.

The U.S.S.R. Inventor Certificate No. 542,523 discloses a balloon catheter wherein a balloon having an elastic contracting member around the mouth of the balloon receives a distal end of a catheter through the mouth of the balloon. Once the balloon is filled, the catheter is retracted from the balloon mouth and the elastic band closes off the mouth of the balloon to maintain the balloon inflated.

Some other patents which provide background art and which disclose various inflatable, balloon-type structures for insertion into a human body are as follows:

U.S. Pat. No. 3,978,1863 to Fettel et al; U.S. Pat. No. 3,993,080 to Loseff; U.S. Pat. No. 4,091,816 to Elam; U.S. Pat. No. 4,149,539 to Cianci; U.S. Pat. No. 4,154,243 to Patel et al; U.S. Pat. No. 4,182,328 to Bolduc et al; U.S. Pat. No. 4,188,954 to Patel et al; and U.S. Pat. No. 4,219,026 to Layton.

As will be described in greater detail hereinafter, the detachable balloon catheter of the present invention provides a miniaturized balloon catheter assembly and a method of using such balloon catheter assembly to efficiently disengage an inflated balloon from a cannula and provides a balloon assembly which is relatively easy and inexpensive to manufacture. In particular, the balloon catheter assembly and its method of use provide a simple to operate, active and stress-free mechanism for detaching with a short burst of pressure, a balloon assembly from a cannula of the balloon catheter assembly.

SUMMARY OF THE INVENTION

According to the present invention there is provided a detachable balloon catheter assembly for use in a blood vessel comprising: a small diameter cannula having a distal end and a proximal end and adapted to be coupled at the proximal end thereof to a source of fluid pressure; a rigid cylinder having a distal end and a proximal end; sealing valve means within said rigid cylinder and positioned at the distal end of said rigid cylinder, the distal end of said cannula being adapted to be inserted into said proximal end of said rigid cylinder and slidably through said sealing valve means; an inflatable balloon fixed to said distal end of said rigid cylinder; said sealing valve means being formed of a resilient material and having a passageway extending therethrough; said passageway being defined by an elongate diametrically and axially extending slit situated in the middle of and extending axially through said sealing valve means prior to insertion of said cannula through said sealing valve means and upon insertion of said cannula through said slit said pasageway takes the form of a cylindrical aperture which provides a fluid tight seal against and around the outer surface of said cannula; said inflatable balloon having a mouth portion at one end thereof coupled to said sealing valve means in said rigid cylinder such that upon inflation of said balloon and upon withdrawal of said cannula from said passageway, said passageway returns to an elongate slit configuration thereby to provide a fluid-tight seal for the now inflated balloon, a piston being mounted on said cannula and being received in the proximal end of said rigid cylinder with the distal end of said cannula being received through said elongate slit; said cannula having a side aperture in the wall thereof between said piston and said sealing valve means whereby, after inflation of said balloon, fluid flows through said side aperture into the space in said rigid cylinder between said sealing valve means and said piston to apply a pressure against said piston in a direction away from said sealing valve means; and means for supplying a burst of pressure through said side aperture to cause detachment of said cannula and said piston from said cylindrical sleeve.

Further according to the invention there is provided a detachable balloon catheter assembly comprising a rigid cylinder having a distal end and a proximal end, a balloon having an open end coupled to said distal end of said rigid cylinder, a valve assembly in said rigid cylinder, a catheter, detachable fluid coupling means including a filling tube connected to said catheter and a piston on said filling tube in said rigid cylinder, said filling tube being initially coupled to said valve assembly within said rigid cylinder, and means for quickly detaching said fluid coupling means from said valve means and said rigid cylinder.

In use, the miniaturized detachable balloon catheter is inserted into a blood vessel and the balloon is inflated until the sides of the balloon are in contact with the walls of the vessel. Thereafter, the cannula which carries the balloon is withdrawn from the balloon and the balloon is sealed to prevent deflation of the balloon. A burst of pressure is used to drive the cannula in a direction away from the inflated balloon in order to detach the cannula from the balloon.

When the cannula is detached from the balloon, a sealing valve closes thereby preventing deflation of the balloon. The sealing valve is formed of a resilient material having an elongated passageway extending therethrough. The passageway takes the form of an elongate slit prior to the insertion of the cannula through the passageway, and upon insertion of the cannula through the passageway, the passageway takes the form of a cylindrical aperture which is in fluid-tight engagement against the outer surface of the cannula while allowing the cannula to easily slide through the passageway.

When the balloon is inflated to a desired size, the cannula may be withdrawn from the passageway thereby causing the passageway to revert to the elongate slit configuration in order to provide a fluid-tight seal for the inflated balloon.

The method of the present invention is carried out with the miniaturized detachable balloon catheter assembly of the present invention in diagnostic and in therapeutic procedures in connection with human blood vessels. The balloon catheter assembly includes a cannula having a small outer diameter adapted for insertion into blood vessels and an inflatable balloon mounted on the distal end of the cannula prior to insertion into the vessel. After insertion of the balloon into the vessel, the balloon is moved to a desired location. A fluid pressure is then applied to the proximal end of the cannula to inflate the balloon. The balloon catheter assembly includes a piston and cylinder type mechanism on the distal end of the catheter responsive to a burst of pressure for detachment of the cannula from the balloon.

When the cannula is detached from the balloon, a sealing valve closes thereby preventing deflation of the balloon. The sealing valve is formed of a resilient material having an elongate passageway extending therethrough. The passageway takes the form of an elongate slit prior to the insertion of the cannula through the passageway, and upon insertion of the cannula through the passageway, the passageway takes the form of a cylindrical aperture which is in fluid-tight engagement against the outer surface of the cannula while allowing the cannula to easily slide through the passageway.

When the balloon is inflated to a desired size, the cannula may be withdrawn from the passageway thereby causing the passageway to revert to the elongate slit configuration in order to provide a fluid-tight seal for the inflated balloon.

The method of the present invention is carried out with the miniaturized detachable balloon catheter assembly of the present invention in diagnostic and in therapeutic procedures in connection with human blood vessels. The balloon catheter assembly includes a cannula having a small outer diameter adapted for insertion into blood vessels and an inflatable balloon mounted on the distal end of the cannula prior to insertion into the vessel. After insertion of the balloon into the vessel, the balloon is moved to a desired location. A fluid pressure is then applied to the proximal end of the cannula to inflate the balloon. The balloon catheter assembly includes a piston and cylinder type mechanism on the distal end of the catheter responsive to a burst of pressure for detachment of the cannula from the balloon.

BRIEF DESCRIPTION OF THE DRAWINGS

FIG. 1 is a plan view with portions broken away of one embodiment of a miniaturized detachable balloon catheter assembly constructed according to the teachings of the present invention;

FIG. 2 is a sectional view of the inflatable balloon and sealing valve assembly of the balloon catheter assembly illustrated in FIG. 1;

FIG. 6 is shown with FIGS. 1 and 2 on the first sheet of drawings and is a sectional view of the sealing valve of the balloon catheter assembly and is taken along line 6—6 of FIG. 5;

FIG. 7 is a plan view with portions broken away of another embodiment of a miniaturized detachable balloon catheter assembly including a unique syringe type drive mechanism connected to the proximal end of a catheter of the balloon catheter assembly all of which are constructed according to the teachings of the present invention;

FIG. 8 is an enlarged cross-sectional view of the balloon and valve assembly juxtaposed to a filling tube assembly at the distal end of the catheter which is received within a cylinder of the balloon and valve assembly, all of which are constructed according to the teachings of the present invention;

FIG. 9 is a perspective view of the syringe type drive mechanism shown in FIG. 7 with portions broken away;

DESCRIPTION OF THE PREFERRED EMBODIMENTS

Figure 3:
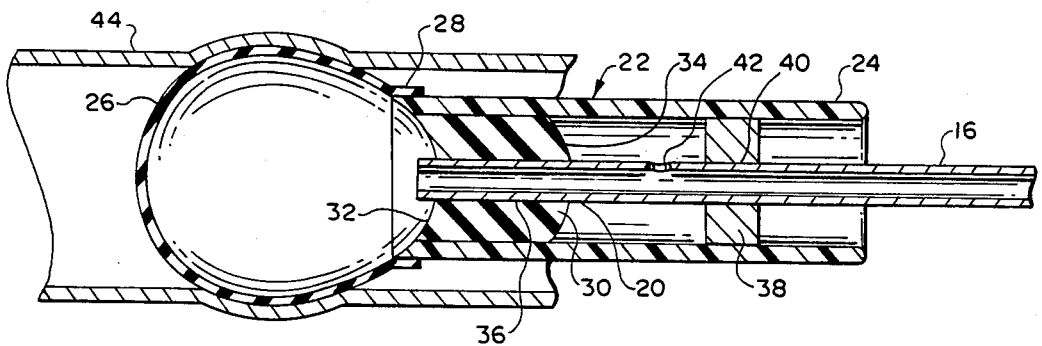
FIG. 3 is a sectional view of the balloon and sealing valve assembly illustrated in FIG. 2 together with a cannula distal end and piston thereon of the balloon catheter assembly and shows the balloon in an inflated configuration within a blood vessel.

FIG. 1 illustrates a detachable balloon catheter assembly 12 connected to a conventional source of pressurized fluid, such as hypodermic syringe 14. The balloon catheter assembly 12 includes an elongate cannula 16 having its proximal end 18 coupled to the hypodermic syringe 14 and its distal end 20 coupled to a balloon and valve assembly 22.

As shown in FIG. 2, the assembly 22 includes a rigid cylindrical sleeve member 24, an inflatable balloon 26 having a mouth portion 28 which is bonded to the distal end of the sleeve member 24 and a sealing valve member 30 which is disposed within the sleeve member 24. More particularly, the mouth portion 28 of the inflatable balloon 26 is adhesively bonded to the periphery of the cylindrical sleeve member 24. The balloon 26 is preferably fabricated from either latex or silicone rubber.

As illustrated, the sealing valve member 30 takes the form of a cylindrical plug 30 having a concave face 32 on the distal end and a convex face 34 on the proximal end. The valve member 30 is formed of a resilient material such as silicone rubber and, as will be described in more detail below, the valve member 30 includes an elongate slit 36 which extends from the distal concave face 32 to the proximal convex face 34. Prior to fabrication of the balloon assembly 22, the inside diameter of the cylindrical sleeve member 24 is smaller than the outside diameter of the resilient sealing valve member 30, thereby causing substantial compressive forces to be applied to the resilient valve member 30 when this component is inserted into the rigid sleeve member 24. The valve member 30 may be adhesively bonded to the inside walls of the sleeve member 24 at the distal end of the sleeve member 24.

The compressive forces which are applied to the periphery of the resilient valve member 30 cause the walls of the slit 36 to conform to the outer periphery of the distal end 20 of the cannula 16 or a filling tube assembly mounted to the distal end 20 of the cannula 16 thereby providing a fluid-tight seal between the valve member 30 and the cannula 16. With this arrangement, however, the cannula 16 frictionally engages the valve member 30 so that the cannula 16 may be withdrawn from the valve member 30.

As shown in FIG. 3, a disc-shaped piston member 38 is disposed about the periphery of the distal end 20 of the cannula 16 and is positioned in spaced relationship to the valve member 30. More particularly, the cannula 16 extends through a coaxial aperture 40 in the piston member 38 and is adhesively bonded to the piston member 38. A passageway 42 extends through the wall of the cannula 16 at a position between the piston member 38 and the valve member 30 so that fluid pressure when applied through the passage of the cannula 16 may be passed through the passageway 42 for driving the piston member 38 in a direction away from the valve member 30.

In a cardiovascular surgical procedure, the balloon catheter assembly 12 is inserted into a blood vessel 44 and the balloon and valve assembly 22 are moved through the blood vessel 44 until a desired site is reached. During placement of the balloon assembly 22, the balloon 26 remains in a configuration as shown in FIG. 2. When the balloon and valve assembly 22 reach a desired position within the vessel 44, fluid pressure is applied by the hypodermic syringe 14 through the cannula 16 to thereby cause the balloon 26 to become inflated as illustrated in FIG. 3. As the balloon 26 becomes inflated, the sides of the balloon contact and seal against the inside wall of the blood vessel 44 thereby sealing off the blood vessel 44.

Figure 4:
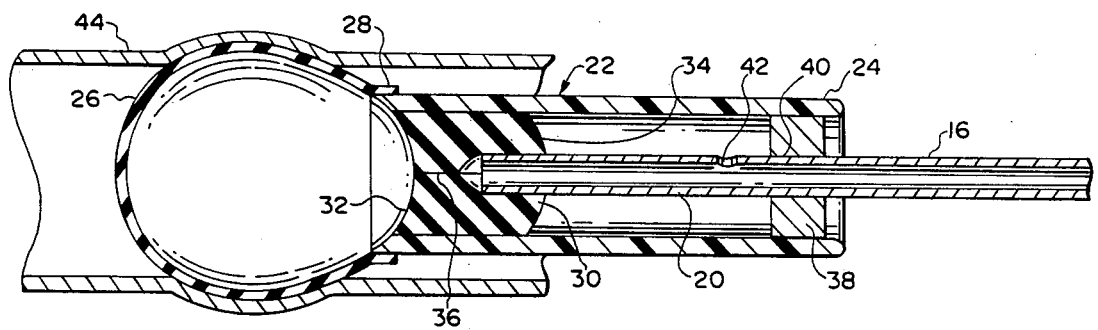
FIG. 4 is a sectional view of the balloon catheter assembly similar to the view shown in FIG. 3 and shows the cannula partially withdrawn from the sealing valve.

As illustrated in FIG. 4, with an increase in fluid pressure once the sides of the balloon 26 come into contact with the walls of the vessel 44, the fluid passes through the passageway 42 in the cannula 16 and is applied against the face of the piston member 38 and an additional burst of pressure is applied to drive the piston member in a direction away from the valve member 30. When the piston member 38 is driven away from the valve member, the distal end 20 of the cannula 16 is withdrawn through the slit 36 thereby permitting the walls of the slit 36 to move back into contact with each other.

Figure 5:
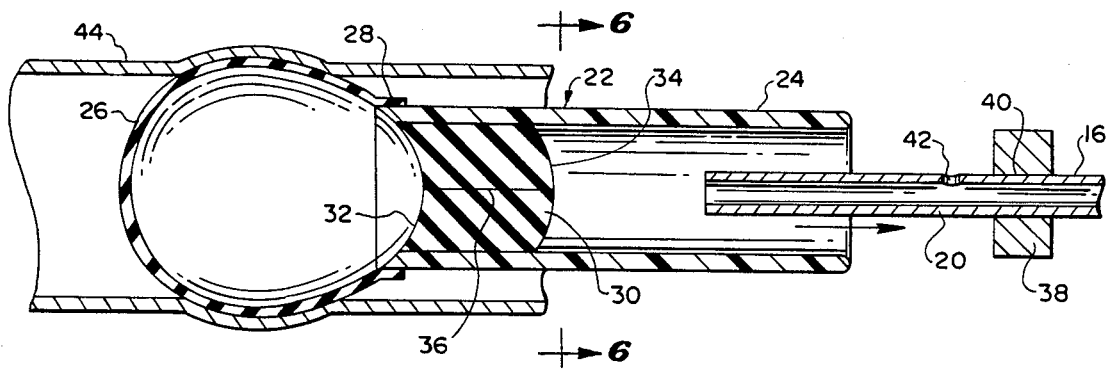
FIG. 5 is a sectional view of the balloon catheter assembly similar to the view shown in FIG. 4 and shows the cannula entirely withdrawn from the sealing valve.

FIG. 5 illustrates the balloon and valve assembly 22 after detachment of the cannula 16. As illustrated in FIGS. 5 and 6, the walls of the slit 36 are then in engagement with each other thereby preventing any leakage of fluid out of the balloon assembly and valve assembly 22.

The compressive forces as previously discussed, tend to enhance the sealing characteristics of the slit 36 after removal of the cannula 16. The concave distal surface of the valve member 30 results in compressive forces being directed in a direction which tends to aid in withdrawal of the cannula 16. The convex face 34 of the sealing valve member 30 causes compressive forces to be generated in a direction which assists in the withdrawal of the cannula 16.

It has been found that in order to achieve an optimum seal between the slit 36 and the cannula 16, the width of the slit 36, as illustrated in FIG. 6, should be approximately equal to one-half of the circumference of the cannula 16. With this arrangement, upon insertion of the cannula 16 into the slit 36, the side walls of the slit 36 tend to conform very precisely to the periphery of the cannula 16 thereby providing an excellent fluid seal.

Referring now to FIG. 7, there is illustrated therein another embodiment of a balloon catheter assembly 100 constructed in accordance with the teachings of the present invention. The balloon catheter-assembly 100 includes a balloon and valve assembly 102 mounted at the distal end 104 of a catheter 106 and a syringe type drive mechanism 108 mounted at the proximal end 110 of the catheter 106.

As shown in FIG. 8, the balloon and valve assembly 102 includes a bullet shaped balloon 112 which can be made of latex or silicone. The balloon 112 has a rounded distal end 114 and an open proximal end 116 which is shown in FIG. 8 as being received around the distal end 118 of a metal cylinder or sleeve 120. If desired, the cylinder 120 can be made of a hard plastic material. In the embodiment shown in FIG. 8, the open end 116 of the latex balloon 112 is received about the outer periphery of the distal end 118 of the cylinder 120 and secured thereto by an appropriate adhesive.

However, as shown in phantom in FIG. 8, it has been found to be preferable to have an open end 116' of the balloon folded downwardly and received within a smaller diameter opening 122 in the distal end 118 of the cylinder 120 and then secured by an adhesive within the distal end 118 of the cylinder 120.

The smaller in diameter opening 122 of the cylinder 120 is formed by an annular shoulder 124 which extends inwardly from the outer periphery of the cylinder 120. As shown, the edge of this opening 122 is rounded so that no sharp edges exist which would cut into the balloon 112.

The cylinder 120 is preferably made of stainless steel such as No. 304 stainless steel and is passivated after the machining thereof.

The metal cylinder 120 has an open proximal end 126 which has an interior bevelled surface 128 that facilitates the insertion of an O-ring 130 into the interior of the cylinder 120 as will be described in more detail below.

Then, the cylinder 120 can be formed with an annular groove 132 which is adapted to receive the O-ring 130 and hold same therein in a less stressed condition as will be described further below.

At the distal end 118 of the metal cylinder 120 adjacent and abutting the shoulder 124 is situated a silicone rubber disc 134 having a valve forming slit 136 through the center thereof extending axially the length of the disc 134 and diametrically in the middle of the disc 134 like the slit 36 shown in FIG. 6. Such slit 136 has a width which is less than the diameter of said disc 134 and which is approximately one-half the circumference of a filling tube received therein (e.g., filling tube 140).

The balloon and valve assembly 102 can be formed in several ways. In one method of forming the balloon and valve assembly 102, the proximal open end 116 of the balloon 112 is inserted through the opening 122, through the metal cylinder 120 and pulled out through the distal end 118 of the cylinder 120 until the proximal end of the balloon 112 extends out the proximal end 126 of the metal cylinder 120. The silicone rubber disc 134 is then fixed within the open end 116 of the balloon 112. Then, the balloon 112 and disc 134 are pulled into cylinder 120 until disc 134 is adjacent or against shoulder 124.

It is contemplated that the valve forming disc 134 and balloon 112 may be formed (a) from two pieces which are then fixed together or (b) an integral one piece unit and then pulled through the proximal end 126 of the cylinder 120 until disc 134 is against shoulder 124.

As shown in FIG. 8, the balloon catheter assembly 100 includes a filling tube assembly 140 which is adapted to be received within the proximal end 126 of the metal cylinder 120 and is utilized first for filling the balloon 112 and second for ejecting the filling tube assembly 140 from the proximal end 126 of the metal cylinder 120.

The filling tube assembly 140 includes a metal filling tube 142 having a swaged distal end 144 which is adapted to be pushed through the slit 136 to be exposed to the interior of the balloon 112 for filling same and having a proximal end 146 which is received within distal end 148 of a soft plastic catheter 106 such as the type sold under the trademark Ducor. Mounted on the metal tube or needle 142 intermediate the ends thereof is a metal piston 152 which has an outer diameter almost equal to the inner diameter of the metal cylinder 120. The metal piston 152 has an annular groove 154 (FIGS. 10, 13, 14) on the outer periphery thereof for receiving the O-ring 130. Just forward of the metal piston 152, the tube 142 has an elongate generally oval opening 156 in a side wall thereof.

The alignment of the annular grooves 132 and 154 with O-ring 130 received in both grooves may provide a locating function for locating the filling tube 142 within the cylinder 120, such that the swaged distal end 144 thereof is pushed sufficiently through the slit 136 within the silicone rubber disc 134 so as to be open to the interior of the balloon 112. Secondly, the elongate oval shaped opening 156 is properly located in space 158 between the back face 165 of the silicone rubber disc 134 and a front face 166 of piston 152 is not pushed into the slit 136 and closed off by the silicone rubber disc 134.

Furthermore, when aligned and in registry, the annular grooves 132 and 154 enable the O-ring 130 normally to be in a less stressed condition. In this respect, long term stressing of elastomers causes permanent distortion and without the annular grooves 132 and 154, compression set of the O-ring 130 would eventually take place and diminish the force holding the piston 152 in the cylinder 120.

The annular groove 132 machined in the cylinder 120 can accept the O-ring 130 and allow the O-ring 130 to expand into the groove 132 with such expansion minimizing compression set and increasing the force of inadvertent detachment. Silicone rubber O-rings having 70 durometer are recommended as well as tougher rubber materials such as buna-N elastomeric material.

In view of the small dimension of cylinder 120, and the resulting difficulty in forming groove 132 thereon, in one preferred embodiment of the assembly 100, the cylinder 120 is formed without the groove 132.

In still another emeobidment, a piston 163 as shown in phantom in FIG. 8 has a longer length and a rounded half moon shaped flange 164 at the proximal end thereof which will bear against the rear edge of the cylinder 120 and in that way provide a proper locating of the swaged distal end 144 of the filling tube 140 and proper locating of the elongate oval shaped opening 156 rearwardly of the back face 165 of disc 134. The flange 164 is larger in diameter than the cylinder 120 and the round rear surface of the flange 164 can provide a guiding function if the assembly 102 has to be withdrawn. In this respect, the round rear surface of flange 164 pushes vessel tissue outwardly to prevent such tissues from engaging or catching on the rear edge of cylinder 120 or the rear edge of the balloon 112.

The length of the filling tube 142 is determined by the length of the side opening 156 in the filling tube 142 and the length of tube required to penetrate through the valve forming slit 136 in the disc 134. To prevent excessive valve distortion, the diameter of the filling tube 142 is kept to a minimum allowable by the viscosity of the balloon filling solution. The filling tube's required pressure drop is increased to the optimum by the swaging of the distal end 144 of the tube that enters the balloon to an opening smaller than the I.D. of the tube 142 and the swaged rounded end 144 of the tube 142 prevents insertion damage to the valve formed by the slit 136.

Also according to the invention the balloon catheter assembly 100 includes the syringe type liquid pressure applying or drive mechanism 108 (FIGS. 7 and 9) which will be described in detail below, for providing a slow filling of the balloon 112 with a fluid or solution such as a radio-opaque solution, followed by a short high pressure burst of fluid or solution for detaching the filling tube assembly 140 from the balloon and valve assembly 102.

Figure 10:
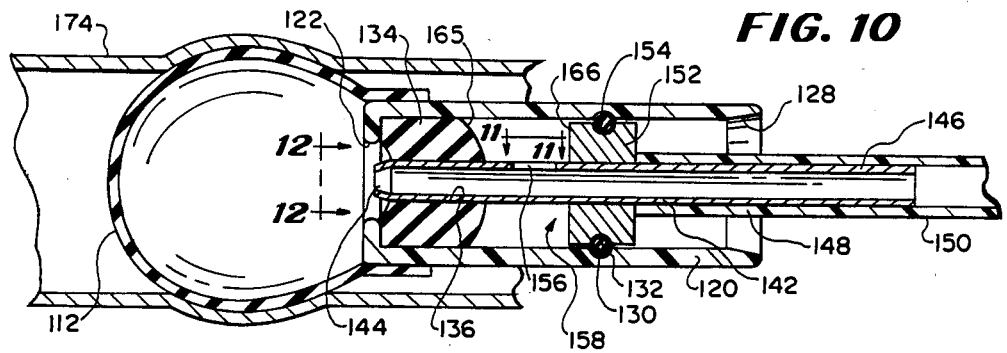
FIG. 10 is a sectional view with portions broken away of the balloon and valve assembly with the filling tube assembly received within the cylinder and the combined assemblies received in a blood vessel.
Figure 11:
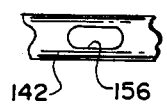
FIG. 11 is a top plan view of a tube of the filling tube assembly mounted at the distal end of the catheter as shown in FIG. 10 and is taken along line 11—11 of FIG. 10.
Figure 12:
FIG. 12 is an end view of the swaged end of the filling tube shown in FIG. 10 and is taken along line 12—12 of FIG. 10.

As shown in FIG. 10, with the filling tube assembly 140 properly received and located within the balloon and valve assembly 102 the syringe type drive mechanism 108 can be actuated by rotating a knurled knob 172 (FIG. 9) thereof for slowly filling the balloon 112 through the end opening 144. At the same time, the filling fluid or liquid is supplied through the side opening 156 to the interior space 158 between the back face 165 of the valve disc 134 and the front face 166 of the piston 152.

After the balloon 112 has been sufficiently filled with the filling material and presses against the sides of a blood vessel 174, thereby closing the blood vessel 174, a trigger button 176 (FIGS. 7 and 9) of the drive mechanism 108 can be depressed thereby to cause a radially extending arm 178 to move circumferentially within an L-shaped slot 180 in a body 182 of the drive assembly 108 to an axially extending portion 184 of the L-shaped slot 180 and move forwardly a short distance in the slot portion 184 under the action of a spring 186 acting against an internal cylindrical member 190 from which the arm 178 extends. This results in a high pressure pulse being exerted on the filling solution or material in space 158 and because of the smaller cross-sectional area of the swaged end opening 144 relative to the cross-sectional area of the side opening 156 in the filling tube 142. This pulse of pressure flows through the side opening 156 into the interior space 158 between the back face 165 of the valve disc 134 and the front face 166 of the piston 152 and causes the piston 152 to move rearwardly from the valve disc 134 out of cylinder 120 thereby disengaging the filling tube assembly 140 from the balloon and valve assembly 102.

The inner diameter of the filling tube 142 and the smaller swaged end diameter opening 144 thereof provide a high pressure drop such that a very small portion of the pressure pulse is transmitted to the balloon 112.

The catheter 106 can then be removed following full detachment of the filling tube assembly 140 from the balloon and valve assembly 102 and the balloon 112 soon aided by the body will form a permanent vascular occlusion.

In order to provide the high pressure drop and appropriate functioning of the piston 152 and the desired detachment of the filling tube assembly 140 from the balloon and valve assembly 102, the ratio of the cross-sectional area of the side opening 156 relative to the cross-sectional area of the swaged end opening 144 is a number between 3:1 and 10:1 and preferably approximately 7:1.

Figure 13:
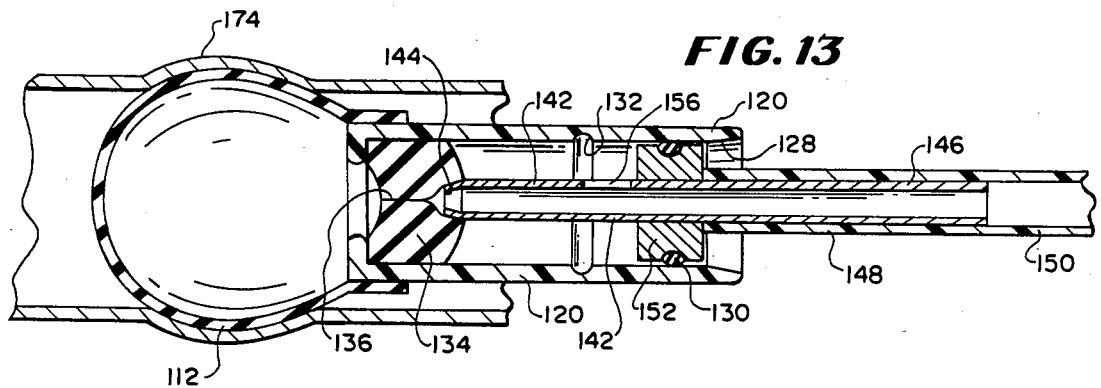
FIG. 13 is a sectional view similar to the view shown in FIG. 10 and shows the filling tube assembly after a pulse of fluid has begun to force the filling tube assembly outwardly of the cylinder of the balloon and valve assembly.
Figure 14:
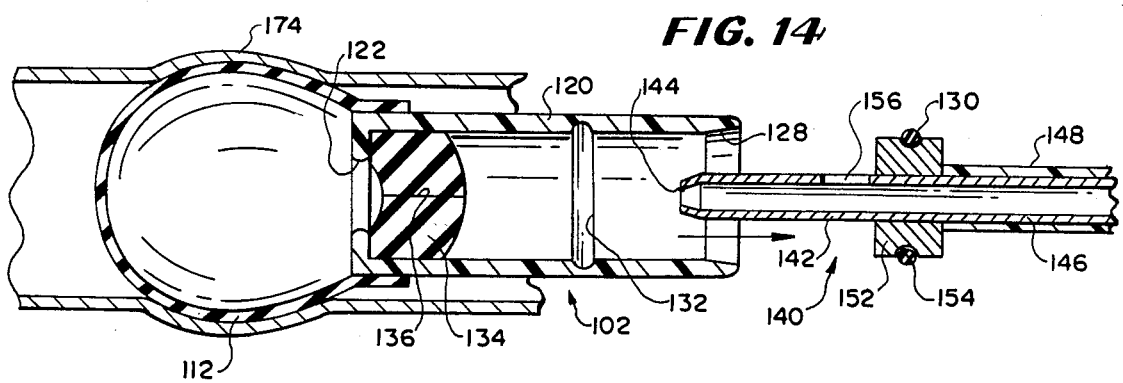
FIG. 14 is a sectional view similar to the sectional view shown in FIG. 13 and shows the filling tube assembly at the distal end of the catheter after it has been expelled from the cylinder of the balloon and valve assembly and shows the valve in the cylinder of the balloon and valve assembly in a sealed closed condition.

The movement of the filling tube assembly 140 after a burst of pressure has been supplied to the interior space 158 is illustrated in FIG. 13 and full detachment of the filling tube assembly 140 is shown in FIG. 14.

Referring now to FIGS. 7 and 9, the proximal end 110 of the catheter 106 is coupled to the drive mechanism 108 by a LEUER brand coupling 193 to a syringe 194 having a finger rest 195 received within a semi-annular slot 196 in a cutaway portion of the body 182 of the syringe drive mechanism 108.

In use, the syringe 194 is first filled with a filling solution. Then the syringe 194 and piston or plunger 197 thereof are nested in the cutaway portion of the body 182 of the drive mechanism 108 with the drive mechanism engaging the piston 197 and the finger rest 195 received in the slot 196. Next, the catheter 102 with balloon and valve assembly 102 attached at the distal end thereof is coupled at 193 to the syringe 194. Air is then purged from the catheter 106 and the balloon 112 through the balloon 112. The balloon and valve assembly 102 are now ready for insertion into the blood vessel 174 and when the balloon is in a desired location in the blood vessel 174, the syringe drive mechanism 108 is operated to inflate the balloon 112.

As shown in FIGS. 7 and 9, the syringe drive mechanism 108 includes a coupling bracket 198 which is received in a cavity 200 in the cutaway portion of the body 182 and around a conventional piston or plunger head 202 mounted at the proximal end of the piston 197. The coupling bracket 198 is mounted at the end of a threaded shaft 204 which is threadedly received in and through the cylindrical member 190. The cylindrical member 190 is slidably received in a second bore 205 and positioned for limited axial and limited radial movement by reason of the radially extending arm 178 received in the L-shaped slot 180. The threaded shaft 204 extends into and has a slidable spline connector within a cylindrical coupling member 206 which is received in a smaller bore 208. The shaft 204 terminates within coupling member 206 and a short rod 210 also has a slidable spline connection with the coupling member 206 and is fixed at its proximal end in a hub 212 within the knurled knob 172.

With this construction, rotation of the knurled knob 172 will cause the rod 210 to rotate coupling member 206 and shaft 204 which rotates within the cylindrical member 190 which is constrained against rotational and axial movement by reason of the arm 178 extending therefrom received in the L-shaped slot 180. In this way, the coupling bracket is slowly advanced to slowly advance the piston 197 into the syringe 194 for moving the filling material or solution into the balloon 112.

Then, when it has been determined, such as by X-ray, that the blood vessel 174 is occluded by the inflated balloon 112 bearing against the interior wall of the blood vessel 174, the operator can push the trigger button 176 inwardly so that a pin 214 connected thereto moves the arm 178 out of a circumferentially or transversely extending leg 216 of the L-shaped slot 180 and in alignment with the axially extending leg 184 of the L-shaped slot 180. At this point the spring 186 which is compressed between a wall 218 in the body 182 and the cylindrical member 190 forces the cylindrical member 190 forward until the arm 178 reaches the forward end of the axially extending leg 184. This results in a short burst of pressure being applied by the portion 197 on the filling solution in the syringe 194 coupled to the catheter 106, which burst is transmitted to the space 158 between the disc 134 and the piston 152 so as to "pop" the filling tube assembly out of the cylinder 120 thereby detaching the filling tube assembly 142 and catheter 106 from the balloon and valve assembly 102.

Fine control of balloon inflation and deflation is accomplished with the syringe type drive mechanism 108 simply by manipulating the knurled knob 172. Then, a pressure pulse can be generated by the trigger release button 176 causing spring 186 to act on the cylindrical member 190 which forces the elongate piston 197 of the syringe type drive mechanism 120 forward.

The spline connection of the threaded shaft 204 permits the shaft 204 to move forwardly within the coupling member 206 without moving the knurled knob 172 forwardly.

In this way, the knurled knob 172 can transmit a torque through the rod 210, and splined coupling member 206 to the threaded shaft 204 and the knurled knob 172 does not move when the spring 186 drives the threaded shaft 204 forward by acting on the cylindrical member 190.

From the foregoing description it will be apparent that the balloon catheter assemblies 12 and 100 of the present invention have a number of advantages, some of which have been described above and others of which are inherent in the invention. In particular, the balloon catheter assemblies of the present invention provide a simple system for effecting a therapeutic embolization useful for cerebral and pulmonary arteriovenous malformations, arterial aneurysms, reduction of vascularity prior to surgery and interruption of blood supply to tumors. More specifically, the balloon catheter assemblies 12 and 100 of the present invention provide for a simple, efficient and effective detachment of a catheter/cannula assembly 16 or 140 from a balloon and valve assembly 22 or 102.

Also from the foregoing description it will be apparent that modifications can be made to the balloon catheter assemblies 12 and 100 of the present invention without departing from the teachings of the present invention. Accordingly, the scope of the present invention is only to be limited as necessitated by the accompanying claims.

I claim:

1. A detachable balloon catheter assembly for use in a blood vessel comprising: a small diameter cannula having a distal end and a proximal end and adapted to be coupled at the proximal end thereof to a source of fluid pressure; a rigid cylinder having a distal end and a proximal end; sealing valve means within said rigid cylinder and positioned at the distal end of said rigid cylinder, the distal end of said cannula being adapted to be inserted into said proximal end of said rigid cylinder and slidably through said sealing valve means; an inflatable balloon fixed to said distal end of said rigid cylinder; said sealing valve means being formed of a resilient material and having a passageway extending therethrough; said passageway being defined by an elongate diametrically and axially extending slit situated in the middle of and extending axially through said sealing valve means prior to insertion of said cannula through said sealing valve means and upon insertion of said cannula through said slit said passageway takes the form of a cylindrical aperture which provides a fluid tight seal against and around the outer surface of said cannula; said inflatable balloon having a mouth portion at one end thereof coupled to said sealing valve means in said rigid cylinder such that upon inflation of said balloon and upon withdrawal of said cannula from said passageway, said passageway returns to an elongate slit configuration thereby to provide a fluid-tight seal for the now inflated balloon, a piston being mounted on said cannula and being received in the proximal end of said rigid cylinder with the distal end of said cannula being received through said elongate slit; said cannula having a side aperture in the wall thereof between said piston and said sealing valve means whereby, after inflation of said balloon, fluid flows through said side aperture into the space in said rigid cylinder between said sealing valve means and said piston to apply a pressure against said piston in a direction away from said sealing valve means; and means for supplying a burst of pressure through said side aperture to cause detachment of said cannula and said piston from said cylindrical sleeve.

2. The balloon catheter assembly of claim 1 wherein the width of said slit is equal to approximately one-half the outer circumference of said cannula.

3. A detachable balloon catheter assembly comprising a rigid cylinder having a distal end and a proximal end, a balloon having an open end coupled to said distal end of said rigid cylinder, a valve assembly in said rigid cylinder, a catheter, detachable fluid coupling means including a filling tube connected to said catheter and a piston on said filling tube in said rigid cylinder, said filling tube being initially coupled to said valve assembly within said rigid cylinder, and means for quickly detaching said fluid coupling means from said valve means and said rigid cylinder.

4. The balloon catheter assembly of claim 4 wherein said valve assembly comprises an elastomeric disc with an axially extending and diametrically extending valve forming slit therein and said filling tube at the distal end of said catheter is received in and through said slit and has an open distal end which is placed in communication with said balloon.

5. The balloon catheter assembly of claim 4 wherein opposite sides of said valve-forming slit conform respectively to the adjacent outer circumferential portions of said filling tube in sufficiently close proximity thereto to create a fluid tight seal between said opposite sides of said slit in said disc and the adjacent circumferential portions of said filling tube received therein.

6. The balloon catheter assembly of claim 5 wherein said slit has a width equal to at least one-half of the circumference of said filling tube.

7. The balloon catheter assembly of claim 4 wherein said cylinder has an inwardly extending annular shoulder at said distal end thereof forming an opening smaller in diameter than the interior of said cylinder, said opening having rounded edges, and said open end of said balloon is received through said opening and fixed within said cylinder.

8. The balloon catheter assembly of claim 7 wherein said open end of said balloon is fixed to the outer surface of said elastomeric disc which is mounted within said cylinder at the distal end thereof.

9. The balloon catheter assembly of claim 4 wherein said piston is received through the proximal open end of said rigid cylinder.

10. The balloon catheter assembly of claim 9 wherein said piston has means for locating said piston in said cylinder.

11. The balloon catheter assembly of claim 10 wherein said locating means include a rear end portion of said piston and a flange on said rear end portion of said piston which abuts a proximal end edge of said cylinder.

12. The balloon catheter assembly of claim 11 wherein said flange has a rounded rear surface and a diameter larger than the diameter of said cylinder whereby said flange can provide a guiding function on withdrawal of said balloon and said valve assembly.

13. The balloon catheter assembly of claim 9 wherein said piston has an O-ring mounted on said piston.

14. The balloon catheter assembly of claim 13 wherein said proximal end of said cylinder has a bevelled inner surface tapering outwardly from the interior of said cylinder for receiving and facilitating insertion and compression of said O-ring on said piston within said cylinder when said piston is inserted into said cylinder to place said O-ring in said annular groove.

15. The balloon catheter assembly of claim 9 wherein said filling tube has a side opening in a sidewall thereof and said opening is on said filling tube between the front face of said piston and the rear face of said elastomeric disc and opens into the space between said elastomeric disc and said piston.

16. The balloon catheter assembly of claim 15 wherein the ratio of the cross-sectional area of the opening at the distal end of said filling tube to the cross-sectional area of said side opening is a number between 1:3 and 1:10.

17. The balloon catheter assembly of claim 16 wherein said ratio is a number equal to approximately 1:7.

18. The balloon catheter assembly of claim 15 wherein said side opening is an oval shaped opening in the side wall of said tube.

19. The balloon catheter assembly of claim 15 wherein said means for quickly detaching said fluid coupling means from said rigid cylinder comprises a syringe type drive means mounted to the proximal end of said catheter for injecting fluid through said catheter into said balloon and into said space between said disc and said piston.

20. The balloon catheter assembly of claim 19 wherein said drive means include means for slowly injecting fluid through said catheter into said balloon and means for applying a burst of pressure to the fluid in said catheter which is transmitted through said side opening to said space between said disc and said piston quickly to force said filling tube assembly out of said cylinder.

21. The balloon catheter assembly of claim 20 wherein said drive means include a body with a cutaway portion for receiving the proximal end of a syringe coupled to said catheter, an elongate piston received in said syringe and having a head at the rear end thereof received in a cavity in the cutaway portion of said body, a metering member having a threaded bore therethrough in said body, holding means within said body normally holding said member in one position in said body and permitting limited axial movement of said metering member, a threaded shaft received in and through said metering member, first coupling means for coupling the forward end of said shaft to said piston head at the rear end of said elongate piston in a manner permitting axial but not necessarily rotational movement of said shaft to apply pressure to said piston, a rotatable member mounted at the proximal end of said body, and second coupling means for coupling the rearward end of said shaft to said rotatable member in a manner permitting axial movement of said second coupling means or said shaft relative to said rotatable member while permitting rotational movement of said rotatable member to be transmitted to said shaft.

22. The balloon catheter assembly of claim 21 wherein said holding means include an arm fixed to and extending radially outwardly from said metering member, said body having an L-shaped slot in the periphery thereof through which said arm extends with the arm positioned at the dead end of the transverse leg of said slot which extends transversely to the axis of said shaft, and a spring in a cavity in said body between a rear wall of said cavity in said body and a rear end of said metering member in said body, which spring urges said metering member forwardly and forms part of said means for applying a burst of pressure.

23. The balloon catheter assembly of claim 22 wherein said means for applying a burst of pressure include trigger means for moving said arm into alignment with the axial leg of said L-shaped slot which extends axially relative to said shaft axis to allow said spring to move said metering member a short distance equal to the length of travel of said arm in said axial leg of said L-shaped slot thereby to apply a burst of pressure to said piston which is transmitted to the fluid in the cannula.

24. The balloon catheter assembly of claim 23 wherein said trigger means include a pin, said body having a passageway extending therein generally transversely of the axis of said arm positioned in said transverse leg of said slot for receiving said pin and a trigger button on the outer end of said pin whereby, on depression of said trigger button, said arm is moved out of said transverse leg into alignment with said transverse leg and said spring pushes said metering member, said threaded shaft, and said piston a short distance to apply a pressure burst to the fluid in said catheter which is transmitted through said side opening to said space between said disc and said piston to force said filling tube assembly out of said cylinder.

25. The balloon catheter assembly of claim 4 wherein the distal end opening of said tube is reduced-in-diameter from the diameter of the interior of said tube such as can be formed by swaging the distal end of said tube which also provides a rounded end of said tube to facilitate insertion of said tube through said slit.

26. The balloon catheter assembly of claim 4 wherein said filling tube is a needle, the proximal end of which is received and fixed within the distal end of said catheter.

27. A method for filling a detachable balloon and valve assembly and then quickly detaching said balloon and valve assembly from the distal end of a catheter in a balloon catheter assembly of the type comprising a balloon fixed to a distal end of a rigid cylinder, a valve member in said rigid cylinder, a filling tube assembly including a filling tube received in the proximal end of the rigid cylinder and having a piston thereon, the tube being received in said rigid cylinder through a valve-forming slit in said valve member in said cylinder and having a distal end opening communicating with the balloon and a side opening communicating with a space between the valve member and the piston, and the tube side opening being larger than the tube end opening, said method comprising the steps of: slowly applying pressure to fluid in said catheter to cause the fluid to fill and inflate said balloon and to fill said space; followed by applying a pressure burst to said fluid in said catheter which is applied through said side opening to said fluid in the space between said valve member and said piston quickly to cause ejection and detachment of the filling tube assembly from the valve member and the rigid cylinder.

28. The method of claim 27 wherein the ratio of the cross-sectional area of the opening at the distal end of the filling tube to the cross-sectional area of the side opening is a number between 1:3 and 1:10.

29. The method of claim 28 wherein said ratio is a number equal to approximately 1:7.

* * * * *

UNITED STATES PATENT AND TRADEMARK OFFICE
CERTIFICATE OF CORRECTION

PATENT NO.   :   4,545,367
DATED        :   October 8, 1985
INVENTOR(S)  :   Charles A. Tucci It is certified that error appears in the above-identified patent and that said Letters Patent is hereby corrected as shown below:

Column 13, line 57, "4" should read --3--.

Signed and Sealed this

Twentieth Day of May 1986

[SEAL]

Attest:

DONALD J. QUIGG

Attesting Officer    Commissioner of Patents and Trademarks